US00PP34193P2

(12) United States Plant Patent
Robacker et al.

(10) Patent No.: US PP34,193 P2
(45) Date of Patent: May 3, 2022

(54) ***ABELIA* PLANT NAMED '00-BC-47-13R'**

(50) Latin Name: ***Abelia* hybrid**
Varietal Denomination: 00-BC-47-13R

(71) Applicant: University of Georgia Research Foundation, Inc., Athens, GA (US)

(72) Inventors: Carol Robacker, Peachtree City, GA (US); Allen Byous, Thomaston, GA (US); Sherrod Baden, Milner, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/317,299

(22) Filed: May 11, 2021

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/02
See application file for complete search history.

*Primary Examiner* — Kent L Bell
(74) *Attorney, Agent, or Firm* — Thomas Horstemeyer, LLP

(57) ABSTRACT

A new and distinctive cultivar of *Abelia* plant named '00-BC-47-13R' characterized by a combination of colorful display due to golden-yellow-green and green foliage that changes from early spring through late fall, relatively short height, and the abundant blooms of white flowers with greyed-orange or red sepals from June through September.

6 Drawing Sheets

Figure 1A:
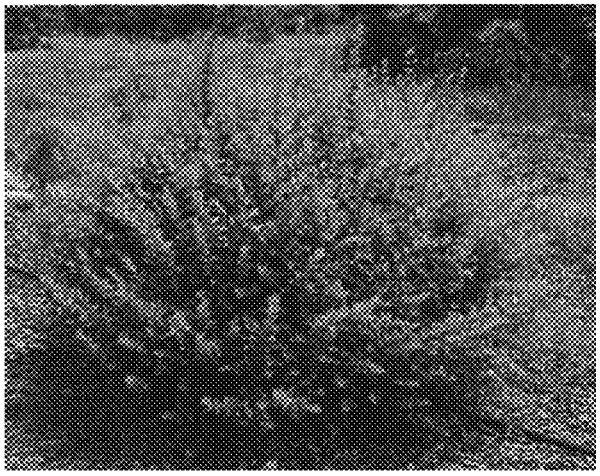
Figure 1B:
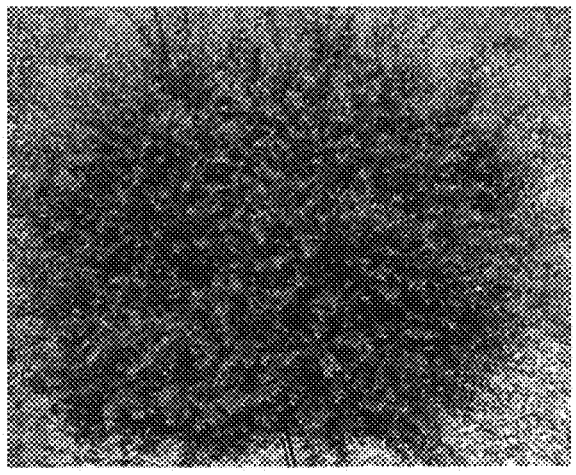
Figure 1C:
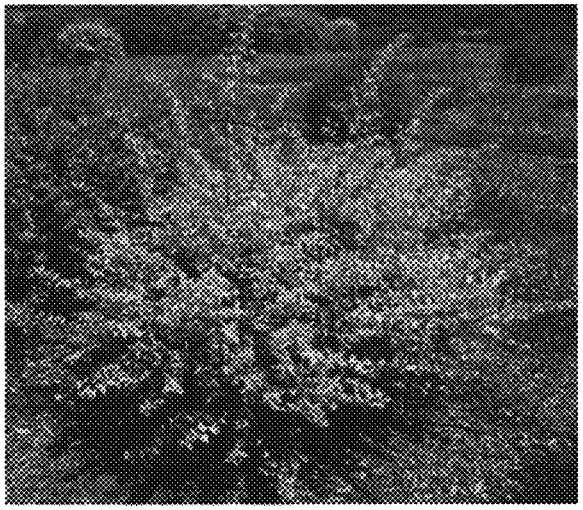
Figure 1D:
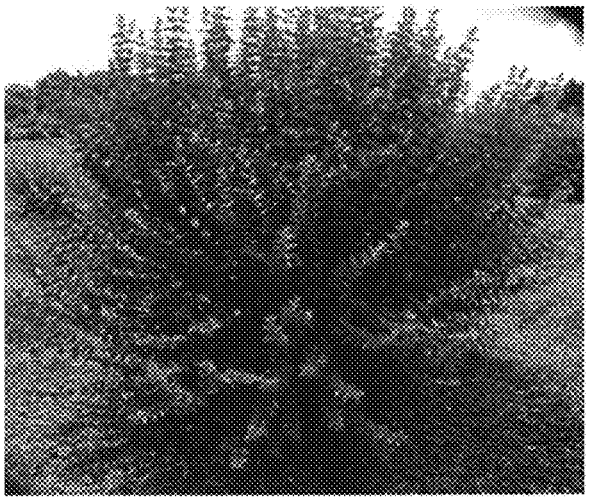

Botanical designation: *Abelia* hybrid.
Cultivar denomination: '00-BC-47-13R'.

BACKGROUND OF THE INVENTION

The present invention relates to a new and distinct cultivar of the ornamental flowering shrub *Abelia* hereinafter referred to by the varietal denomination '00-BC-47-13R'.

The new *Abelia* '00-BC-47-13R' is a product of a planned breeding program conducted by the inventors in Griffin, Ga. The objective of the *Abelia* breeding is to produce a tough and adaptable drought-tolerant plant with commercial value. The new '00-BC-47-13R' has significant commercial and home gardener appeal with its multicolored foliage, colorful sepals, and heavy blooming. These and other qualities are enumerated herein.

The new '00-BC-47-13R' originated from a cross in 1999 between an *Abelia* hybrid '99-2-8' (unpatented, female parent) and an *Abelia grandiflora* 'Francis Mason' (unpatented, male parent). The female parent *Abelia* '99-2-8' originated from a cross in 1998 between an unnamed *Abelia chinensis* plant of unknown origin (unpatented, female grandparent) and *Abelia grandiflora* 'Francis Mason' (unpatented, male grandparent).

Seedlings from the cross between the female parent *Abelia* '99-2-8' and the male parent *A. grandiflora* 'Francis Mason' were planted in a field plot in Griffin, Ga. (cold hardiness zone 8a) in the fall of 2003. Plants were evaluated for flowering and foliage characteristics, plant form and height, cold hardiness and drought tolerance. Plant '00-BC-47-13R' was selected and vegetatively propagated by stem cuttings in Griffin, Ga. In the summer of 2014, three replicates of '00-BC-47-13R' were planted into a field plot in Griffin, Ga. In summer of 2015, two replicates of '00-BC-47-13R' were planted into a field plot in Blairsville, Ga.

(cold hardiness zone 7a), along with 4 other selections in a randomized complete block design.

The original seedling plant has been evaluated in Griffin for 17 years; the asexually propagated '00-BC-47-13R' plants have been evaluated in Griffin for 6 years and in Blairsville for 5 years. In Griffin, plants were pruned every two years to a height of 40 to 50 cm with height and width data collected prior to pruning. First bloom dates were recorded each year. Winter cold and spring frost damage was assessed each spring in Griffin and Blairsville. Observation for disease or insect damage was continuous throughout the summer. Asexual reproduction of the new *Abelia* '00-BC-47-13R' by softwood stem cuttings since 2014 has shown that the unique features of this new *Abelia* are stable and reproduced true to type in successive generations.

SUMMARY OF THE INVENTION

The new *Abelia* cultivar '00-BC-47-13R' has not been observed under all possible environmental conditions. The phenotype may vary somewhat with variations in environment and cultural practices such as temperature, water and fertility levels, soil types, and light intensity without, however, any variance in genotype.

*Abelia* is a genus of 15-30 species and interspecific hybrids that are popular landscape plants. They range from deciduous to evergreen, depending upon the cultivar and the climate. They have attractive, colorful foliage and flower from late spring to autumn. *Abelia* is a low-maintenance shrub that is tolerant of any well-drained soil, has heat and drought tolerance and is resistant to most pests. It thrives in full sun or part shade, and can generally be grown in cold hardiness zones 5 through 9. The new plant is expected to be distributed for landscape use in the U.S. and perhaps in other countries.

Figure 5A:
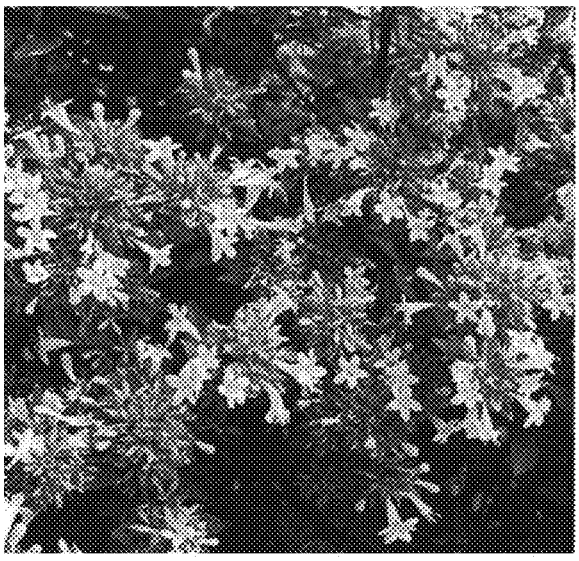
Figure 5B:
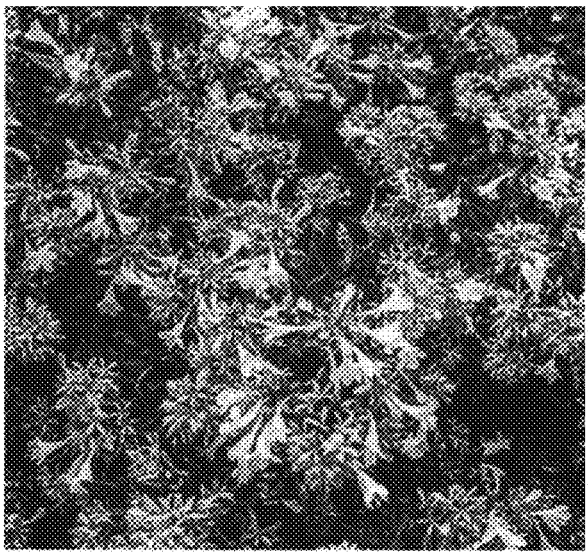
Figure 5C:
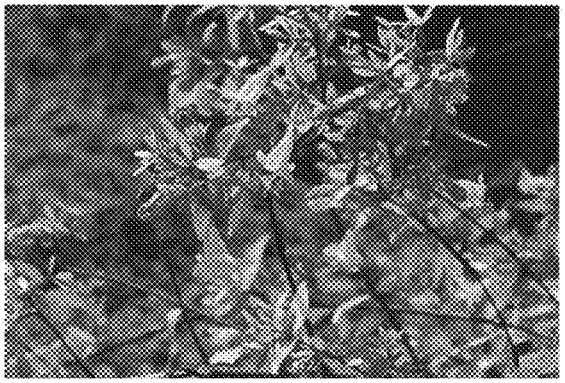

The following traits have been consistently observed in the original and asexually propagated plants of this new variety in both Blairsville and Griffin, Ga., and to the best knowledge of the inventors, their combination are determined to be the unique and distinguishing characteristics of the new *Abelia* cultivar named '00-BC-47-13R'. In combination, these traits set '00-BC-47-13R' apart from all other existing varieties of *Abelia* known to the inventors:

1. colorful display of multi-colored foliage that changes from early spring through late fall, and the abundant blooms of white flowers with orange or red sepals throughout the summer (see all FIGS.);
2. foliage changes from bright golden-yellow-green and green in the spring, to bright green and yellow-green in the summer to yellow-green in the fall (see all FIGS.)
3. shorter height than its parents and many other cultivars, though taller than cultivar '00-BC-47-7R' (see Table 1);
4. heavy blooming with showy compound panicles (FIG. 3A);
5. flowering beginning in late May and continuing throughout the summer in Griffin, Ga. (Table 2); and
6. white flowers with greyed-orange sepals in mid-summer turning to orange-red in late summer (FIG. 5A, Tables 5, 6).

Comparison: The new variety of *Abelia* '00-BC-47-13R' can be compared to its male parent 'Francis Mason' and maternal grandparent *A. chinensis* and to '00-BC-47-7R' (U.S. Plant application Ser. No. 17/317,291), a sibling cultivar. The female parent *Abelia* hybrid '99-2-8' was never propagated or sold, and the plant was discarded in 2001. It is known that '99-2-8' had yellow foliage, a leggy growth habit, and severe photobleaching making the foliage unattractive. The new *Abelia* '00-BC-47-13R' differs from '99-2-8' at least in that it has a shorter height and does not have photobleaching, but further comparison data is not available.

'00-BC-47-13R' plants have been evaluated in field plots in Griffin, Ga. and in Blairsville, Ga. One plant of *A. chinensis* (maternal grandparent) and 'Francis Mason' (paternal parent) have been grown in Griffin since 2001. 'Francis Mason' was asexually propagated, and six replicates were planted in Blairsville in 2003 and six replicates were planted in Griffin in 2009. '00-BC-47-7R', a new release from this breeding program, was used as a standard for comparison as it is a sibling to '00-BC-47-13R'. One plant of '00-BC-47-7R' was planted in Griffin in 2003, with replicates planted in Griffin in 2008, and in Blairsville in 2011. Height and width data were collected in Griffin every year. Plants were pruned every two years. First bloom dates were recorded each year. Winter cold and spring frost damage was assessed each spring in Griffin and Blairsville. Observation for disease or insect damage was continuous throughout the summer.

Foliage of '00-BC-47-13R' is bright golden-yellow-green and green in early summer, changing to a mix of bright green and yellow-green in the summer and yellow-green in the fall. 'Francis Mason has golden yellow foliage from spring through fall; *A. chinensis* has green foliage from spring through fall; and '00-BC-47-7R' has yellow-green to green in June and dark green in the summer and fall (see all FIGS.).

Height of pruned '00-BC-47-13R' is statistically shorter than 'Francis Mason' and *A. chinensis* but taller than '00-BC-47-7R' (Table 1). Width of '00-BC-47-13R' is similar to '00-BC-47-7R' and smaller than 'Francis Mason' and *A. chinensis* (Table 1).

Figure 3A:
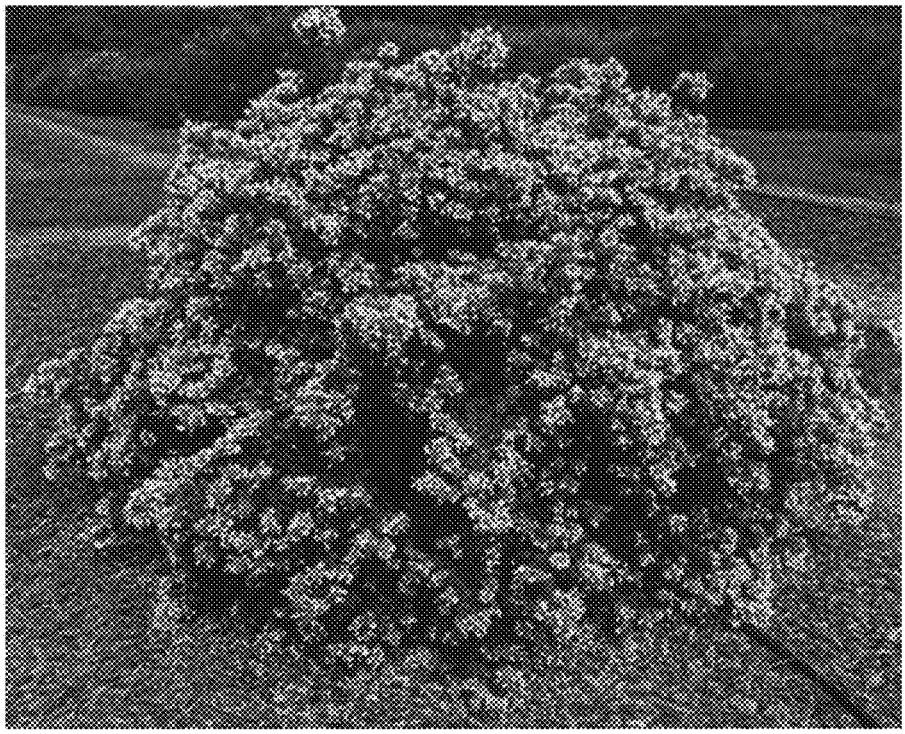
Figure 3B:
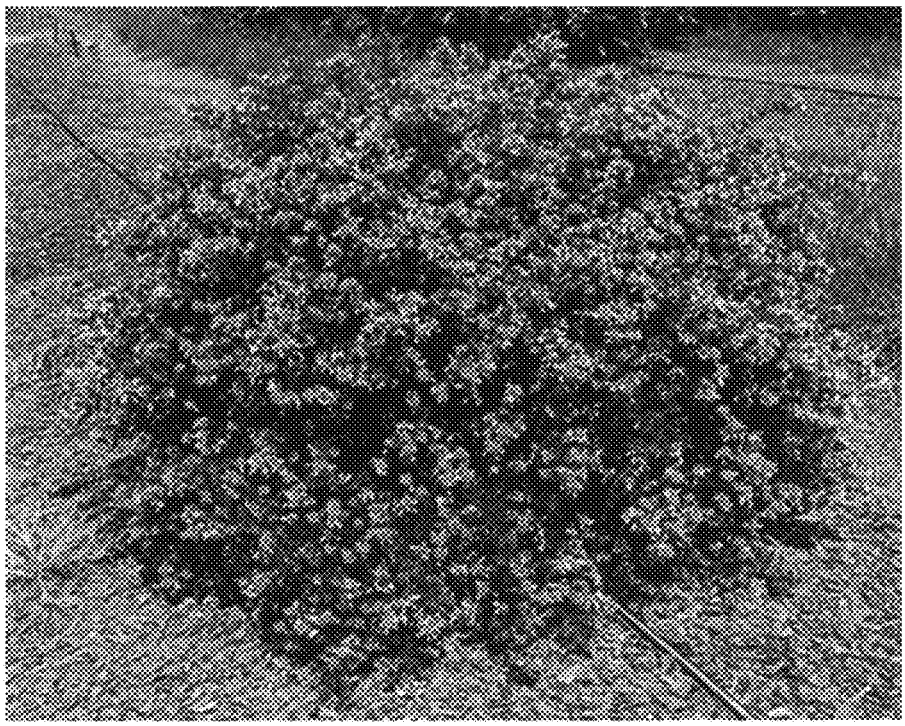
Figure 3C:
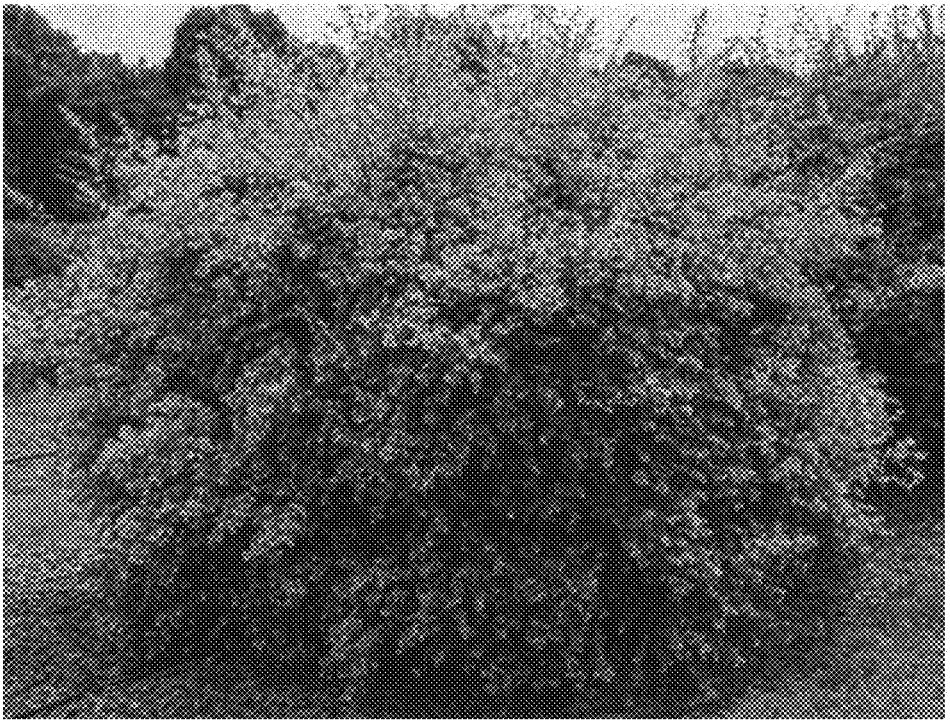

The variety '00-BC-47-13R' usually begins blooming about one week later than '00-BC-47-7R' and two weeks later than 'Francis Mason' but about two weeks earlier than *A. chinensis* (Table 2). The variety '00-BC-47-13R' blooms from late May to September, with heavy blooming in June through August in Griffin (FIG. 3A)

The flowers of '00-BC-47-13R' occur in compound panicles, mostly terminal though some are axillary. The panicles of '00-BC-47-13R' average about 36 cm in length and 24 cm width, similar in length to '00-BC-47-7R' but less wide. The length and width of 'Francis Mason' is significantly greater than that of '00-BC-47-13R', while *A. chinensis* is both shorter and narrower than '00-BC-47-13R' (Table 3, FIGS. 5A-5D). The number of subpanicles per compound panicle averages about 31 on '00-BC-47-13R', which is fewer than that of 'Francis Mason' and '00-BC-47-7R' and greater than *A. chinensis* (Table 3). Subpanicle length of '00-BC-47-13R' is similar to that of 'Francis Mason' and '00-BC-47-7R', though *A. chinensis* is shorter. Subpanicle width of '00-BC-47-13R' is similar to all the check cultivars. Internode length of '00-BC-47-13R' is less than that of 'Francis Mason' and '00-BC-47-7R', but greater than *A. chinensis* (Table 4, FIGS. 5A-5D).

Flowers of '00-BC-47-13R', 'Francis Mason', *A. chinensis*, and '00-BC-47-7R' are white (Table 5); sepals of '00-BC-47-13R' are greyed-orange in mid-summer and orange-red in late summer (FIG. 5A); 'Francis Mason' is greyed-red in mid-summer and orange-red in late summer (FIG. 5C); *A. chinensis* is greyed-red and yellow-green in mid-summer and greyed-orange and yellow-green in late summer (FIG. 5D); and '00-BC-47-7R' is greyed-orange with a yellow-green base in mid-summer and late summer (FIG. 5B) (Table 6). Flowers of '00-BC-47-13R' are similar in length to 'Francis Mason' and '00-BC-47-7R' and longer than *A. chinensis*. Flower width of '00-BC-47-13R' is narrower than 'Francis Mason' and wider than '00-BC-47-7R', but similar to *A. chinensis* (Table 5).

Plants of '00-BC-47-13R' in the Griffin field plot had minor or moderate cold/frost damage in 2015, a winter that was very cold, with a low of 9.6° F. in January and a late spring freeze of 26.2° F. in late March. Minor, moderate or severe damage was also observed on plants of 'Francis Mason in 2015. All five plants of '00-BC-47-7R' had minor damage that year. No damage occurred on *A. chinensis*. No damage occurred on '00-BC-47-13R' or *A. chinensis* in 2017, 2018 or 2019. 'Francis Mason' had four plants with minor damage in 2017 and '00-BC-47-7R' had one plant with minor damage in 2019 (Table 7). Both plants of '00-BC-47-13R' planted in Blairsville Ga. (Zone 7a) in 2015 have survived and are growing well.

As established, three checks were used for comparison to '00-BC-47-13R': parents 'Francis Mason' and *A. chinensis*, and sibling '00-BC-47-7R'. All are distinctly different. Plant '00-BC-47-13R' is shorter in height than its parents and taller than '00-BC-47-7R' (Table 1). The variety '00-BC-47-13R' usually begins blooming about one week later than '00-BC-47-7R' and two weeks later than 'Francis Mason' but about two weeks earlier than *A. chinensis* (Table 2). Panicle length is similar to '00-BC-47-7R', but shorter than 'Francis Mason' and longer than *A. chinensis*. Panicle width is narrower than '00-BC-47-7R' and 'Francis Mason' and wider than *A. chinensis* (Table 3). The number of subpanicles per compound panicle on '00-BC-47-13R' is fewer than that of 'Francis Mason' and '00-BC-47-7R' and greater than *A. chinensis* (Table 3). Subpanicles are longer than *A. chinensis* and internode length on the subpanicle is intermediate to the checks (Table 4). All have white flowers (FIGS. 5A-5D, Table 5). Flowers of '00-BC-47-13R' are similar in length to 'Francis Mason', '00-BC-47-7R' and longer than *A. chinensis*. (Table 5). Sepals of '00-BC-47-13R' are greyed-orange in mid-summer and orange-red in late summer; 'Francis Mason' is greyed-red in mid-summer and orange-red in late summer; *A. chinensis* is greyed-red and yellow-green in mid-summer and greyed-orange and yellow-green in late summer; and '00-BC-47-7R' is greyed-orange with a yellow-green base in mid-summer and late summer (FIGS. 5A-5D, Table 6).

The new *Abelia* '00-BC-47-13R' is readily propagated through cuttings. Six-inch cuttings taken in May or early June before flowering rooted at a rate of over 70%. After 2 months, cuttings can be transferred to one-gallon containers using a well-drained potting mix. From cutting to saleable plant is about 8 months. No insect or disease problems have been noted in potted plants maintained outside the greenhouse, or in field plants. Once established, the plants are quite drought resistant. After landscape establishment, a hard pruning is recommended in early spring approximately every other year to encourage compact growth and heavy blooming.

The new variety '00-BC-47-13R' has colorful foliage that changes from bright golden-yellow-green and green in the spring, to bright green in the summer to yellow-green in the fall. White flowers and greyed-orange to orange-red sepals are borne on showy compound panicles from late May throughout summer.

TABLE 1

Height and width (cm) of '00-BC-47-13R', 'Francis Mason', *A. chinensis* and '00-BC-47-7R' in a field plot in Griffin, GA in November 2019. Plants were pruned every two years to a height of about 40 to 50 cm, depending upon the maturity of the plant. Data are from plants that had been pruned in November 2017, and had been in the field at least 5 years. One plant of each of '00-BC-47-13R' and '00-BC-47-7R was planted in 2003, and reps of '00-BC-47-13R' were planted in 2014. Reps of '00-BC-47-7R' were planted in the field in 2008. One plant of each of 'Francis Mason' and *A. chinensis* was planted in 2001, and reps of 'Francis Mason' were planted in 2009 and 2011.

| Genotype | Rep # | Height (cm) | Width (cm) |
|---|---|---|---|
| '00-BC-47-13R' | 3 | 149.7 ± 9.7* | 196.8 ± 17.2 |
| 'Francis Mason' | 3 | 167 ± 5.1 | 240 ± 5.3 |
| *A. chinensis* | 1 | 256 | 308 |
| '00-BC-47-7R' | 3 | 116 ± 4.4 | 203.2 ± 7.1 |

*Standard error of the means at the 95% confidence level.

TABLE 2

Week of first bloom for '00-BC-47-13R', 'Francis Mason', *A. chinensis* and '00-BC-47-7R' in a Griffin field plot in 2011, 2015, 2017 and 2019. The number in parentheses is the number of plants that bloomed on that date.

| Genotype | 2011 | 2015 | 2017 | 2019 |
|---|---|---|---|---|
| '00-BC-47-13R' | 5-23 (1) | 6-1 (2); 6-8 (2) | 5-29 (1); 6-5 (2) | 5-20 (1); 5-27 (2) |
| 'Francis Mason' | 5-9 (4) | 5-18 (6) | 5-1 (1); 5-8 (4); 5-15(1) | 5-13 (4); 5-20 (2) |
| *A. chinensis* | 6-6 (1) | 6-15 (1) | 6-5 (1) | 6-17 (1) |

TABLE 2-continued

Week of first bloom for '00-BC-47-13R', 'Francis Mason', *A. chinensis* and '00-BC-47-7R' in a Griffin field plot in 2011, 2015, 2017 and 2019. The number in parentheses is the number of plants that bloomed on that date.

| Genotype | 2011 | 2015 | 2017 | 2019 |
|---|---|---|---|---|
| '00-BC-47-7R' | 5-9 (1); 5-16 (5) | 5-25 (1); 6-1 (2); 6-8 (2) | 5-15 (5) | 5-20 (3); 5-27 (2) |

TABLE 3

Comparison of morphological traits of compound panicles of '00-BC-47-13R', 'Francis Mason', *A. chinensis* and '00-BC-47-7R'. Data were collected from field-grown plants in full sun in Griffin, Georgia on Jun. 16 or Jul. 30, 2020, depending upon time of full bloom.

| Cultivar | Compound panicle length[1] (mm) | Compound panicle width[1] (mm) | Number of subpanicles per compound panicle |
|---|---|---|---|
| '00-BC-47-13R' | 359.9b[2] | 241.0b | 30.6b |
| 'Francis Mason' | 457.6a | 389.5a | 55.5a |
| *A. chinensis* | 181.6c | 163.6c | 20.3c |
| '00-BC-47-7R' | 367.0b | 330.5a | 73.5a |

[1]Length and width of compound panicles and number of subpanicles were measured on the ten longest compound panicles on plants of similar age.
[2]Means of lengths and widths were compared across genotypes using t-tests. Means followed by different letters are significantly different $P < 0.05$.

TABLE 4

Comparison of morphological traits of subpanicles of '00-BC-47-13R', 'Francis Mason', *A. chinensis* and '00-BC-47-7R'. Data were collected from field-grown plants in full sun in Griffin, Georgia on Jun. 16 or Jul. 30, 2020, depending upon time of full bloom.

| Cultivar | Subpanicle length[1] (mm) | Subpanicle width[1] (mm) | Internode length on subpanicle[1] |
|---|---|---|---|
| '00-BC-47-13R' | 100.8a2 | 40.1a | 20.7b |
| 'Francis Mason | 110.5a | 40.5a | 26.9a |
| *A. chinensis* | 55.2b | 42.4a | 17.8c |
| '00-BC-47-7R' | 98.8a | 39.0a | 24.3a |

[1]Length and width of compound panicles and number of subpanicles weremeasured on the ten longest compound panicles on a plant of similar age.
[2]Means of lengths and widths were compared across genotypes using t-tests. Means followed by different letters are significantly different $P < 0.05$.

TABLE 5

Flower color and size of '00-BC-47-13R', 'Francis Mason', *A. chinensis* and '00-BC-47-7R'.

| Cultivar | Petal-upper surface | Petal-lower surface | Flower length[1] (mm) | Flower Width[1] (mm) |
|---|---|---|---|---|
| '00-BC-47-13R' | White NN155D | White NN155D | 15.3a | 9.7b |
| 'Francis Mason' | White N155B | White N155B | 16.3a | 11.9a |
| *A. chinensis* | White NN155D | White N155B | 13.1b | 8.9bc |
| '00-BC-47-7R' | White NN155C | White NN155C Red-Purple 62D | 15.1a | 8.4c |

[1]Means of flower lengths and widths were compared across genotypes using t-tests. Means followed by different letters are significantly different $P < 0.05$.

TABLE 6

Sepal color of '00-BC-47-13R', 'Francis Mason', *A. chinensis* and '00-BC-47-7R'.

| Cultivar | Mid-summer | Late-summer |
|---|---|---|
| '00-BC-47-13R | Greyed-Orange 173A | Orange-Red N34C |
| 'Francis Mason' | Greyed-Red 179C | Orange-Red 35C |
| *A. chinensis* | Greyed-Red 179C; Yellow-Green 144B | Greyed-Orange 174C; Yellow-Green 145A |
| '00-BC-47-7R' | Greyed-Orange 175A with 144C Yellow-Green base | Greyed-Orange 173A; Yellow-Green 145A |

TABLE 7

Number of plants of '00-BC-47-13R' and check cultivars with cold or frost damage in the Griffin field plot in 2015, 2017, 2018 and 2019. Plants were classified as having no damage, or minor, moderate or severe damage.

| Cold/frost damage | Year | '00-BC-47-13R' | 'Francis Mason' | *A. chinensis* | '00-BC-47-7R' |
|---|---|---|---|---|---|
| None | 2015 | 0 | 0 | 1 | 0 |
| | 2017 | 3 | 3 | 1 | 5 |
| | 2018 | 3 | 8 | 1 | 5 |
| | 2019 | 3 | 8 | 1 | 4 |
| Minor | 2015 | 3 | 4 | 0 | 5 |
| | 2017 | 0 | 4 | 0 | 0 |
| | 2018 | 0 | 0 | 0 | 0 |
| | 2019 | 0 | 0 | 0 | 1 |
| Moderate | 2015 | 1 | 2 | 0 | 0 |
| | 2017 | 0 | 0 | 0 | 0 |
| | 2018 | 0 | 0 | 0 | 0 |
| | 2019 | 0 | 0 | 0 | 0 |
| Severe | 2015 | 0 | 1 | 0 | 0 |
| | 2017 | 0 | 0 | 0 | 0 |
| | 2018 | 0 | 0 | 0 | 0 |
| | 2019 | 0 | 0 | 0 | 0 |

Notes: Winter of 2015 had a minimum temperature of 9.6° F. in January as well as several days of 15° F. in January and February. A late spring freeze of 26.2° F. occurred on Mar. 29. Winter 2017 was relatively mild, with a minimum cold temperature of 14.5° F. on Jan. 8. A late spring freeze occurred on Mar. 15 and 16, with temperatures of 26.8 and 23.1F respectively. Winter of 2018 was cold in January, with temperatures ranging from 10.9° F. to 17.5° F. on six days that month. February was warm, though 25.8° F. occurred on Mar. 9. Fall was mild. Winter 2019 was warm. The minimum temperature was 20.8° F. on Jan. 30. Fall was mild.

BRIEF DESCRIPTION OF THE PHOTOGRAPHS

The accompanying colored photographic illustrations show the overall appearance and distinct characteristics of the new cultivar of *Abelia* '00-BC-47-13R' showing the colors as true as possible. Colors in the photographs may differ slightly from the color values cited in the detailed botanical description, which accurately describes the colors of the new *Abelia* '00-BC-47-13R'. The photographs were taken of plants grown outdoors in Griffin, Ga. on various dates as noted below.

The photographs labeled FIGS. 1A-1D depict the overall plant habit and foliage color in late spring/early summer of '00-BC-47-13R' (FIG. 1A) as compared to '00-BC-47-7R' (FIG. 1B), 'Francis Mason' (FIG. 1C), all taken on Jun. 3, 2020, and *A. chinensis* (FIG. 1D) taken on Jun. 18, 2020.

Figure 2A:
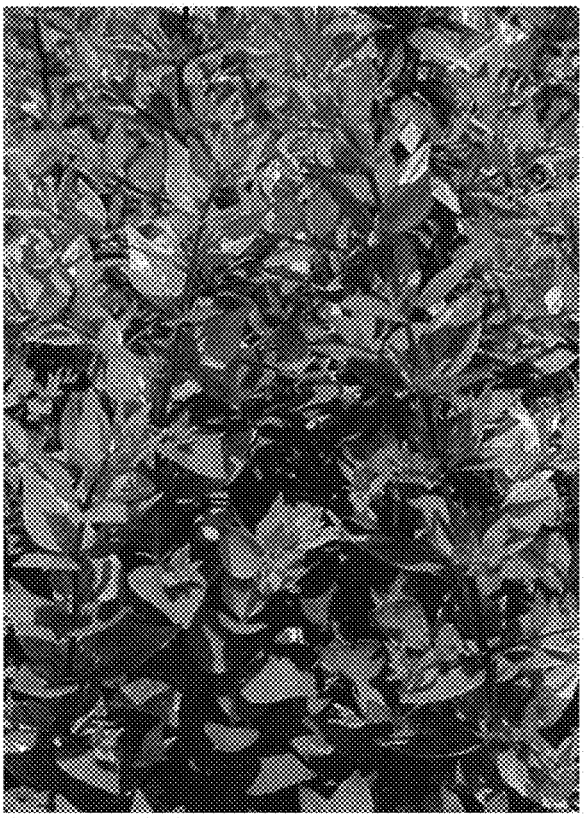
Figure 2B:
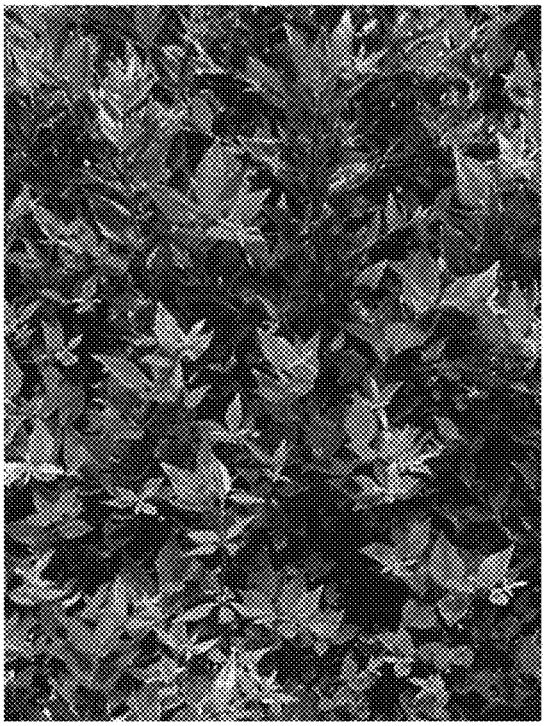
Figure 2C:
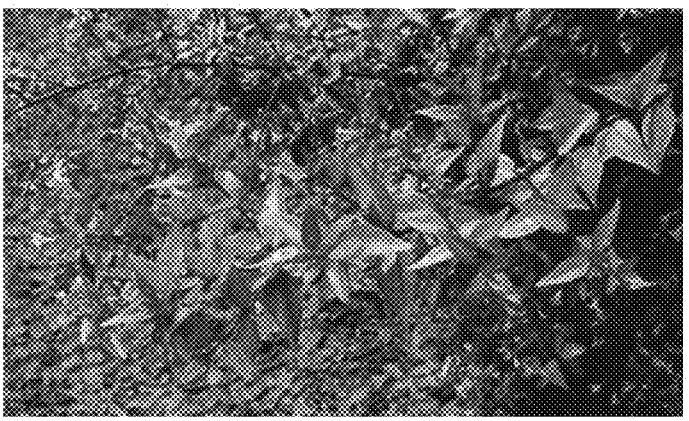
Figure 2D:
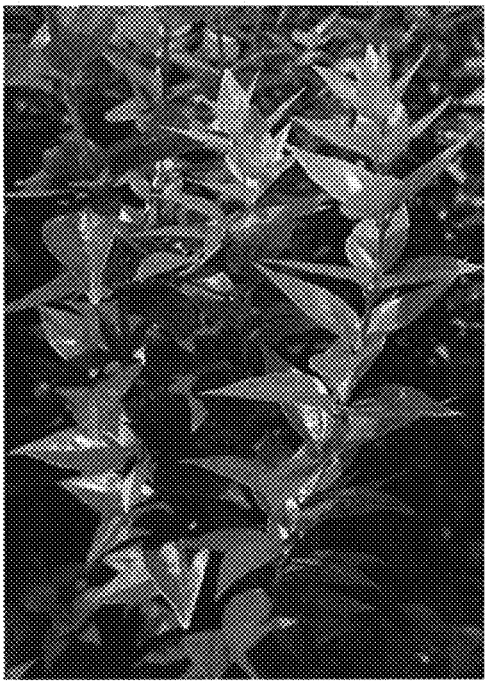

The photographs labeled FIGS. 2A-2D depict close-up views of the early summer foliage of '00-BC-47-13R' (FIG. 2A) as compared to '00-BC-47-7R' (FIG. 2B) (FIGS. 2A and 2B taken on Jun. 3, 2020, 'Francis Mason' (FIG. 2C, taken Jun. 18, 2020), and *A. chinensis* (FIG. 2D, FIGS. 2C and 2D taken Jun. 18, 2020).

Figure 3D:
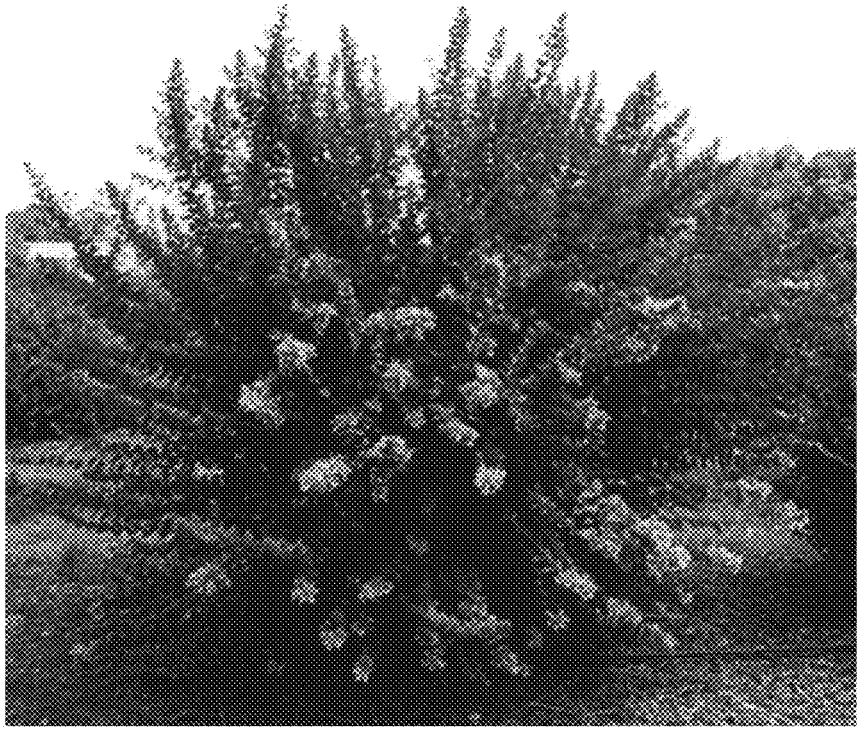

The photographs labeled FIG. 3A-3D depict full bloom of '1 00-BC-47-13R' (FIG. 3A, taken Aug. 27, 2020), '00-BC-47-7R' (FIG. 3B, taken Jul. 23, 2020), 'Francis Mason' (FIG. 3C, taken Jun. 18, 2020), and '*A. chinensis*' (FIG. 3D, taken Jul. 23, 2020).

Figure 4A:
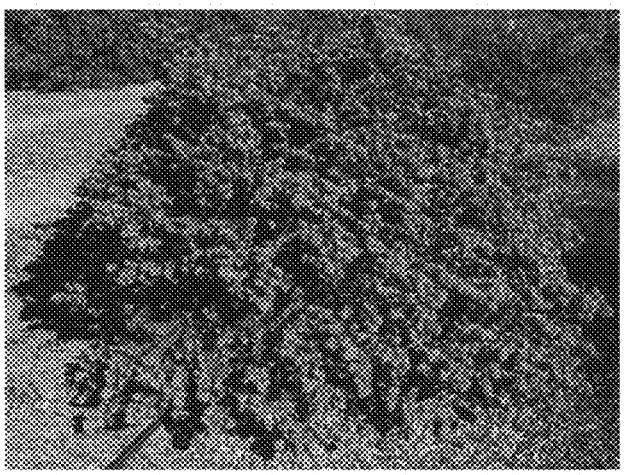
Figure 4B:
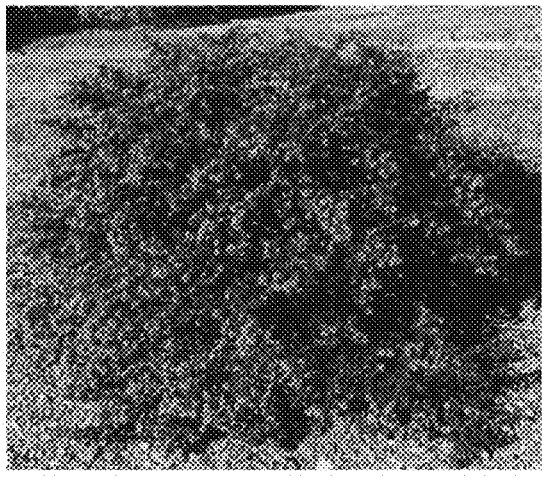
Figure 4C:
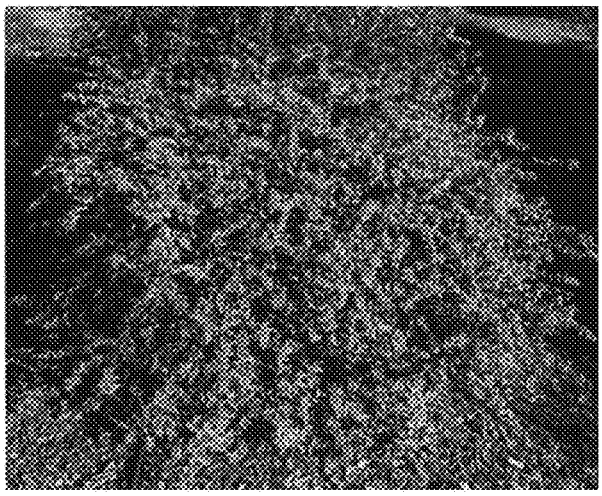
Figure 4D:
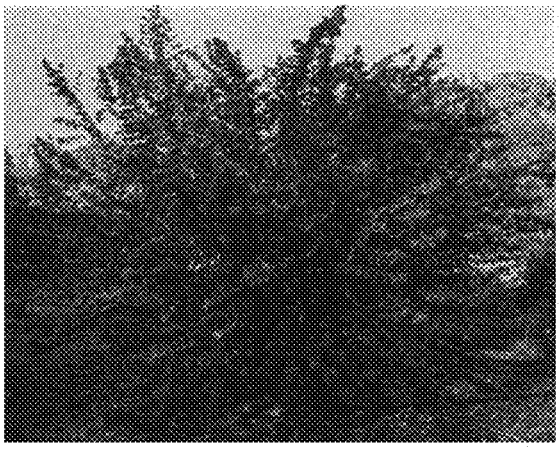

The photographs labeled FIGS. 4A-4D depict fall color of '00-BC-47-13R' (FIG. 4A) compared to '00-BC-47-7R' (FIG. 4B), 'Francis Mason' (FIG. 4C), and *A. chinensis* (FIG. 4D). All photos taken on Nov. 12, 2020.

Figure 5D:
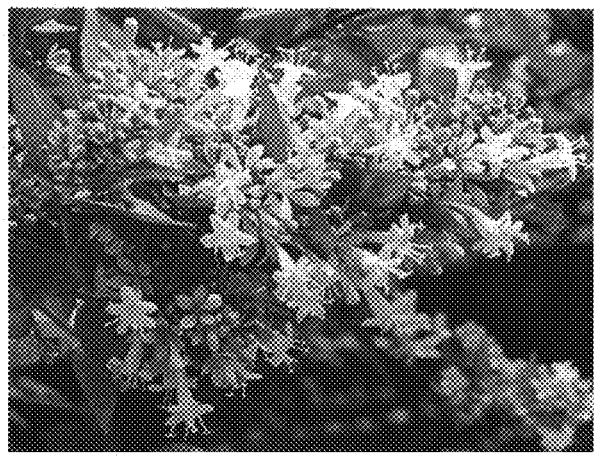

The photographs labeled FIGS. 5A depict close-up views of the flowers and sepals of '00-BC-47-13R' (FIG. 5A, taken Aug. 27, 2020), compared to '00-BC-47-7R' (FIG. 5B, taken Aug. 27, 2020), 'Francis Mason' (FIG. 5C, taken Jun. 18, 2020), and *A. chinensis* (FIG. 5D, taken Jul. 23, 2020).

DETAILED BOTANICAL DESCRIPTION

The following traits have been consistently observed in the original plant of this new variety and in asexually propagated progeny grown from stem cuttings in Griffin and Blairsville, Ga., and, to the best knowledge of the inventors, their combination forms the unique characteristics of the new variety '00-BC-47-13R'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Abelia* cultivar named '00-BC-47-13R'. Where dimensions, sizes, colors, and other characteristics are given, it is to be understood that such characteristics are approximations and averages set forth as accurately as practicable.

Data were collected from '00-BC-47-13R' plants propagated from softwood stem cuttings and grown in one-gallon containers prior to planting in field plots in Griffin, Ga. Data are from plants planted and grown in the field since 2003 and 2014. The average low temperatures for the year ranges from about 38° F. in January to 72° F. in July, and the average high temperature for the year ranges from about 54° F. in January to 88° F. in July for Griffin. In Blairsville, the average low temperature ranges from about 29° F. in January to 62° F. in July and the average high ranges from 45° F. in January to 84° F. in July.

Botanical classification: *Abelia* '00-BC-47-13R'.

*Commercial classification.*—Shrub.

*Parentage.*—Cross between an *Abelia* hybrid plant labeled '99-2-8' (unpatented female parent, which originated from a cross between an unnamed *Abelia chinensis* plant and unpatented plant *A. grandiflora* named 'Francis Mason') and an *Abelia grandiflora* 'Francis Mason' (unpatented male parent).

Growth and propagation:

*Propagation type.*—By softwood stem cuttings.

*Growth rate.*—Softwood cuttings rooted in 3 weeks at an approximate temperature of about 80° F. under the mist.

*Root description.*—White, dense, freely branched.

*Rooting habit.*—Fibrous.

Plant description:

*Form.*—Partially deciduous shrub that retains about 50 to 70% of its leaves, with heavy blooming of white flowers and greyed-orange and orange-red sepals.

*Habit.*—Spreading, upright.

*Usage.*—Various uses, such as container patio plants, potted plants, landscape uses such as border, hedge, and mass planting.

*Vigor.*—Moderately vigorous.

*Size of plant.*—A. Height: about 1.5 m on plants in field for 5 years. B. Width: about 2 m on plants in field for 5 years.

*Stem.*—Mostly upright, mature branches arching. A. First year. 1. Color (RHS): Greyed-Orange 165A. 2. Diameter: about 2 mm; length: about 79 cm. 3. Pubescence: covered in minute curved hairs. 4. Exfoliation/Texture: smooth. 5. Shape: Round. 6. Pith. a. Type: solid. b. Diameter: (measured halfway from apex to start of one year's growth) about 1.5 mm. c. Color (RHS): Yellow-Green 153A. 7. Odor (of bruised stem): Cut grass (faint). 8. Lenticels. a. Number: none observed. 9. Internode length (average of about 5-10 internodes in middle of first year shoots) about 30 mm. 10. Strength: very strong. B. Second Year. 1. Color (RHS): Grey-Brown 199A and 199B. 2. Diameter: about 2.5 mm. 3. Exfoliation/Texture: Mostly smooth, developing lengthwise cracks along stem.

*Vegetative buds.*—A. Arrangement: opposite alternating at different nodes. B. Type: valvate. C. Size (length×width): about 0.5 mm×0.5 mm. D. Scale Number: about 2, sometimes 3. E. Scale Color (RHS): Greyed-Red 181B. F. Position/Disposition (angle to stem): about 45°. G. Number at Node: about 2 vegetative single. H. Pubescence: scattered, very short hairs. I. Shape: lanceolate.

*Leaf scar.*—A. Shape: rounded crescent. B. Vascular Bundle Traces (number, orientation): three horizontal across scar. C. Pubescence: sparse, around scar margin. D. Position of Bud (on leaf scar): about 45° in axis. E. Color Differentiation (RHS): Greyed-Orange 165A. F. Size (h×w): about 1 mm×1 mm.

*Trunk or large stems.*—A. Color(s) (RHS): Greyed-Orange 175D with Greyed-Orange 163C striations. B. What Size Stem Exfoliation beings on: about 3 mm. C. Diameter: about 10-20 mm. D. Texture: longitudinal cracks, striated.

*Leaf.*—A. Leaf type: simple. B. Color Through Season (always RHS). 1. Emerging: April. Upper: Yellow-Green 151A with slight blush Red-Purple 58B on leaf margin; Lower: Yellow-Green 144C. 2. Summer: July. Upper: Green N137B; Lower: Yellow-Green 144B. 3. Fall: November. Upper: Yellow-Green 146A, tips Yellow-Green. 144A or Greyed Orange N167B; Lower: Yellow-Green 146C. 4. Winter: December. Upper: Yellow-Green 146A with Greyed-Orange 173A tips; Lower: Yellow-Green 148B. C. Mature size (L×W): about 3.5 cm×about 1.8 cm; thickness: 0.3 mm. D. Apex: Acute. E. Base: rounded, equilaterail. F. Margin: slightly crenate. G. Shape: lanceolate. H. Lobes (present/absent): absent. I. Vein color (RHS): Yellow-Green 146B. J. Pubescence: 1. Upper Surface: mostly smooth. 2. Lower surface: short hairs concentrated along lower one-half of the midvein; single row of hairs around leaf margin. K. Arrangement on stem: mostly opposite. L. Venation: simple alternate. M. Texture: Degree of waxiness of surface: slightly waxy. N. Odor when crushed: faint grassy.

*Petiole.*—A. Length: about 3 mm. B. Shape: curved and concave. C. Color (RHS): Yellow-Green 144A. D. Pubescence: sparse short, curved hairs mostly on posterior. E. Diameter: about 1 mm.

*Inflorescence(s).*—A. Type: Compound panicle, terminal and axillary. B. Number per Plant: about 500 to 1000, depending upon size of mature plant. C. Size (L×W): single inflorescence about 3×3 cm to 4×4 cm; subpanicle, about 10×4 cm; compound panicle, about 36 cm×24 cm; about 31 subpanicles per compound panicle. D. Color (RHS): 1. At emergence: White NN155D. 2. Full bloom: White NN155D. 3. Fading: White NN155D. E. Longevity: June to frost. F. Peduncle. 1. Length: about 6 mm. 2. Diameter: about 1 mm. 3. Color (RHS): Greyed-Orange 165A. 4. Pubescence: covered in very short hairs. 5. Strength: strong. 6. Aspect: about 45° to stem.

*Flower.*—A. Number per Inflorescence: about 15-100 in various stages of bloom, many panicles and subpanicles. B. Axillary or Terminal: both. C. Symmetry: regular, actinomorphic. D. Size (l×w): about 15 mm×10 mm; Depth: about 10 mm. E. Pubescence: outside, short glandular hairs; inside, short glandular hairs with longer hairs extending into calyx throat. F. Texture: punticulate. G. Color at peak bloom (RHS): 1. Upper surface: White NN155D. 2. Lower surface: White NN155D. H. Fragrance: moderately sweet. I. Time of full maturity: late spring. J. Time range for showiness: late May until early fall. K. Bud: 1. Size (l×w): about 12 mm×2.5 mm. 2. Shape: elongated teardrop. 3. Color (RHS): Red-purple 69C and Red-Purple 73B. 4. Pubescence: covered in tiny glandular hairs. 5. Longevity: 1 week. L. Petals: 1. Number: one. 2. Size (l×w): about 15 mm×10 mm. 3. Shape: funnel, slightly tubular, gamopetalous. 4. Apex: usually 5 lobes, rounded and slightly curled. 5. Base: funnel shaped with short tube about ¼ the length of the flower. 6. Margin: entire but slightly curled. 7. Color at peak bloom (RHS): upper surface: White NN155D; lower surface: White NN155D. 8. Texture: punticulate. 9. Arrangement: N/A. M. Pedicels: 1. Color (RHS): Greyed-Orange 164A. 2. Pubescence: covered in short glandular hairs. 3. Length: about 1-2 mm. 4. Aspect: about 45° to peduncle. 5. Strength: medium. 6. Diameter: about 1 mm. N. Sepal(s): 1. Number: five. 2. Size (l×w): about 5mm×1 mm. 3. Shape: obelliptic. 4. Apex: rounded. 5. Base: attenuate. 6. Margin: entire, smooth. 7. Texture: slightly punticulate. 8. Pubescence: sparse, short hairs, single row around margin. 9. Color at peak of bloom (RHS): a. Upper surface: Grayed-Orange 173A. b. Lower surfaces: Greyed-Orange 173A. O. Male reproductive structures: 1. Number: 4. 2. Anther: a. Size (l×w): about 1 mm×0.5 mm. b. Shape: dorsifixed, linear. c. Color (RHS): White 155C. d. Texture/pubescence: slightly punticulate. 3. Filament: a. Size (l×w): about 12-13 mm×0.2 mm. b. Color (RHS): White 155C. c. Texture: smooth with short hairs towards base. 4. Pollen: a. Quantity: moderate. b. Pollen color (RHS): White N155B. P. Female Reproductive structures: 1. Pistil: a. Shape: monostylus free. b. Size (l×w): about 13 mm×0.5 mm. c. Position: epigynous, ovary inferior. d. Color (RHS): White 155C. e. Pubescence: scattered short hairs, more numerous towards base. 2. Stigma: a. Shape:

circular, domed. b. Color (RHS): White 155C. c. Pubescence: punticulate surface has short, clear papillose structures. 3. Style: a. Length: about 12 mm. b. Shape: tubular. c. Color (RHS): White 155C. d. Pubescence: scattered, short hairs, more numerous toward base. 4. Ovary: a. Shape: oval. b. Number: 1. c. Pubescence: none.

*Fruit*.—A. Type: achene. B. Size (l×w): about 5 mm×1.5 mm. C. Color(s) during ripening (RHS): all stages present during bloom season. 1. Early: (June) Green 144B. 2. Mid: (August) Green 144A. 3. Late: (November) Grey-Brown N199A. D. Shape: grooved cylindrical capsule. E. Number per infructescence: 1. F. Pubescence: covered in short, curved hairs. G. Number of carpels: 1. H. Persistence (effective period): summer to frost.

Disease/pest resistance: No notable diseases or other pest problems have been observed for the new *Abelia* '00-BC-47-13R' that are not also common for other varieties. Plants of the new *Abelia* '00-BC-47-13R' have been observed to have similar resistance to diseases and pests as standard for the genus.

It is claimed:

1. A new and distinct cultivar of *Abelia* plant named '00-BC-47-13R' as illustrated and described herein.

* * * * *